(12) United States Patent
Gagliardoni et al.

(10) Patent No.: US 9,220,883 B2
(45) Date of Patent: Dec. 29, 2015

(54) MEDICAL CONNECTOR

(75) Inventors: Giancarlo Gagliardoni, Estado Miranda (VE); Giuseppe Antonio Nichetti, Pandino (IT); Matteo Ageno, Vimodrone (IT)

(73) Assignee: CEDIC S.R.L., Peschiera Borromeo (MI) (IT)

( * ) Notice: Subject to any disclaimer, the term of this patent is extended or adjusted under 35 U.S.C. 154(b) by 15 days.

(21) Appl. No.: 13/823,500

(22) PCT Filed: Oct. 5, 2010

(86) PCT No.: PCT/EP2010/064863
§ 371 (c)(1),
(2), (4) Date: Mar. 14, 2013

(87) PCT Pub. No.: WO2012/034601
PCT Pub. Date: Mar. 22, 2012

(65) Prior Publication Data
US 2013/0184688 A1    Jul. 18, 2013

(30) Foreign Application Priority Data
Sep. 14, 2010 (WO) ................. PCT/EP2010/063500

(51) Int. Cl.
*A61M 25/16* (2006.01)
*A61M 25/18* (2006.01)
*A61M 39/10* (2006.01)

(52) U.S. Cl.
CPC ... *A61M 39/1011* (2013.01); *A61M 2039/1027* (2013.01); *A61M 2039/1033* (2013.01); *A61M 2039/1044* (2013.01); *A61M 2039/1094* (2013.01); *Y10T 29/49826* (2015.01)

(58) Field of Classification Search
CPC ............. A61M 2039/1027; A61M 2039/1033; A61M 2039/1044; A61M 2039/1094; A61M 39/1011
USPC .......................................... 604/533, 535, 538
See application file for complete search history.

(56) References Cited

U.S. PATENT DOCUMENTS

| 5,507,733 | A  * | 4/1996 | Larkin et al. ................... 604/534 |
| 6,419,670 | B1 * | 7/2002 | Dikeman ....................... 604/533 |
| 2003/0120260 | A1 | 6/2003 | Chu et al. |
| 2007/0076401 | A1 * | 4/2007 | Carrez et al. .................. 361/816 |
| 2008/0147012 | A1 | 6/2008 | Rome |
| 2009/0240178 | A1 | 9/2009 | Hanlon et al. |

(Continued)

FOREIGN PATENT DOCUMENTS

| FR | 2863162 A1 | 6/2005 |
| GB | 2379253 A | 3/2003 |

(Continued)

*Primary Examiner* — Rebecca E Eisenberg
(74) *Attorney, Agent, or Firm* — Jansson Munger McKinley & Kirby Ltd.

(57) ABSTRACT

The present invention provides a connector (1, 2) for use in fluid driving applications such as enteral feeding sets, catheters, and other medical devices, comprising a body (3) having a cylindrical coupling portion (7) with a substantially circular coupling surface (8) and having an outer surface (9) extending from the coupling surface (8) to form an internal cavity (11), a tube mating portion (13) extending outward from the body (3) for connecting to a tube, at least one thread sector (15) provided at the coupling portion (7), and at least one locking means (17) on the coupling portion (7), and at least one locking means (17) on the coupling surface (8).

15 Claims, 6 Drawing Sheets

(56) References Cited

U.S. PATENT DOCUMENTS

2009/0292273 A1 11/2009 Racz et al.
2011/0266796 A1* 11/2011 Monroe et al. ................ 285/361

FOREIGN PATENT DOCUMENTS

| GB | 2451891 A | 2/2009 |
| WO | 2010079396 A1 | 7/2010 |

* cited by examiner

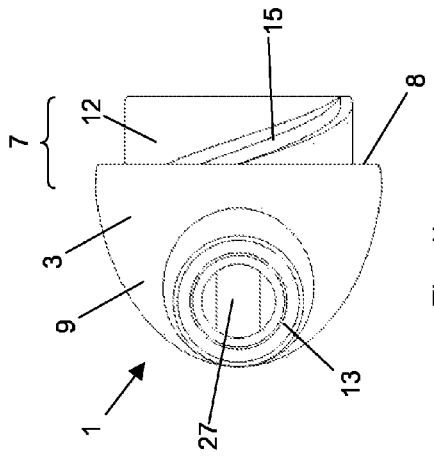
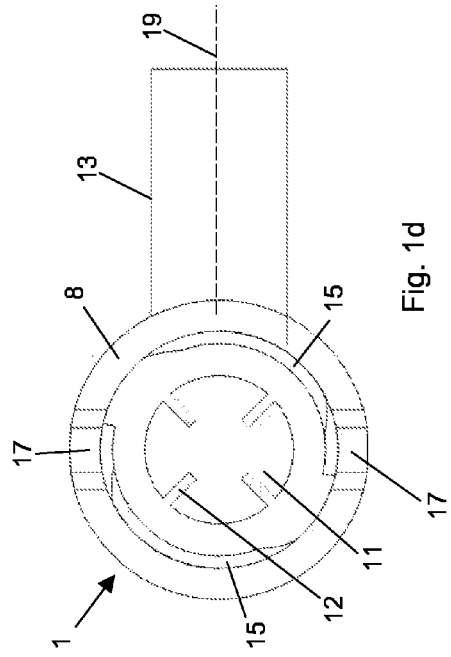
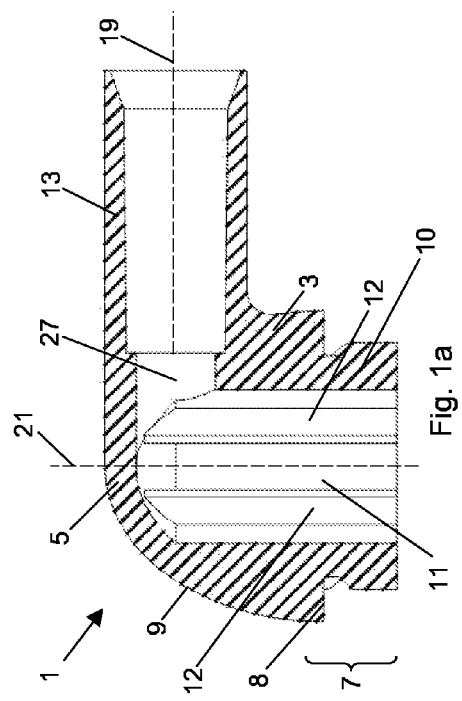
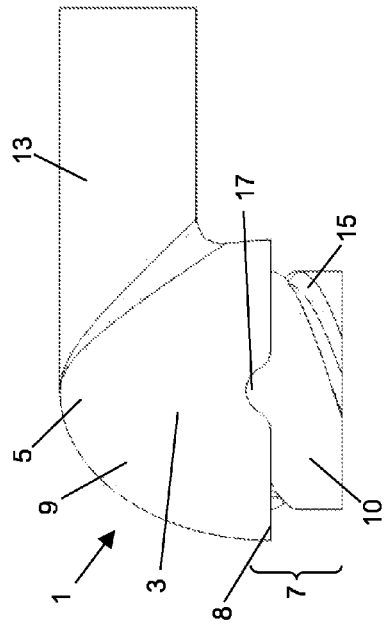

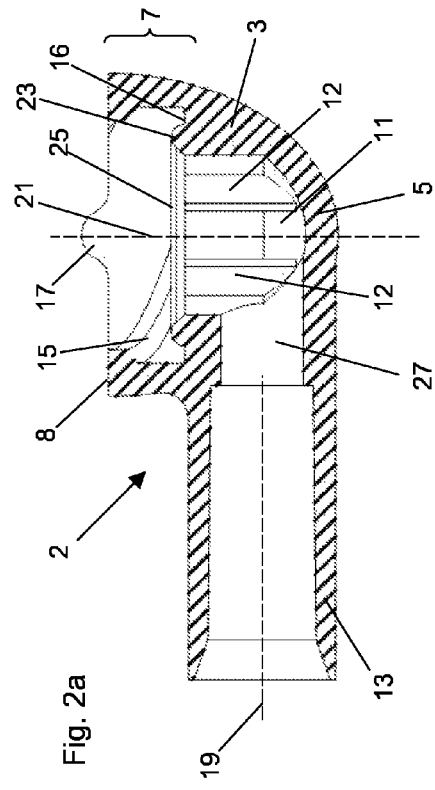
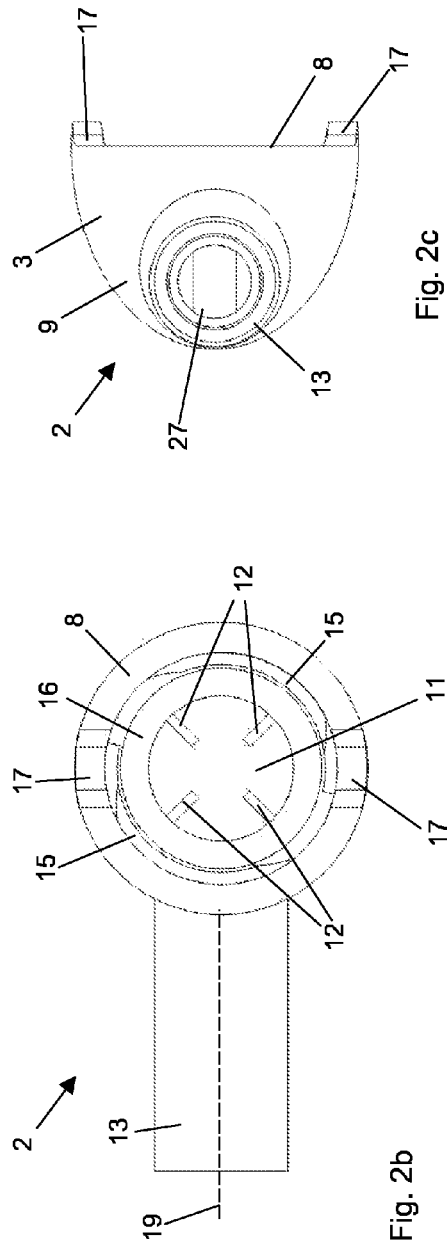

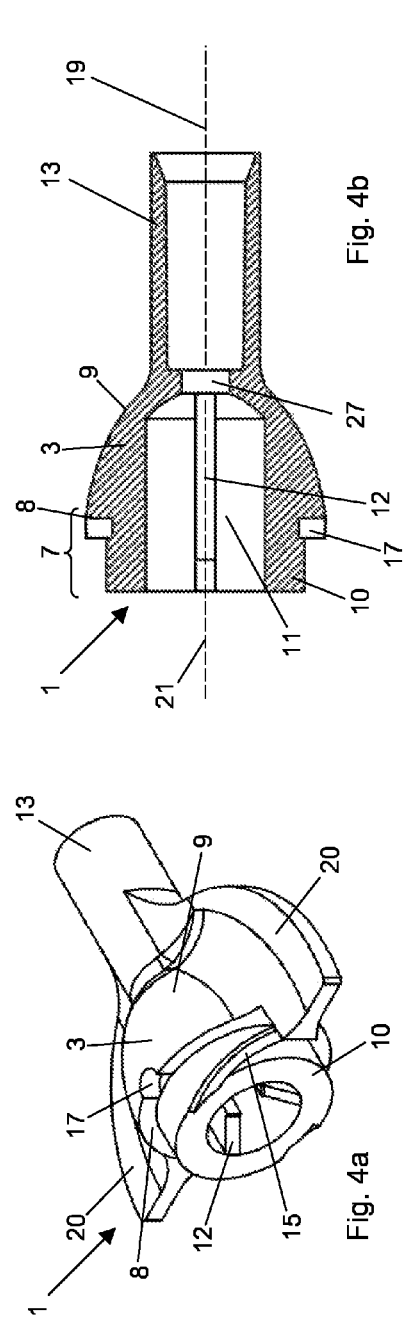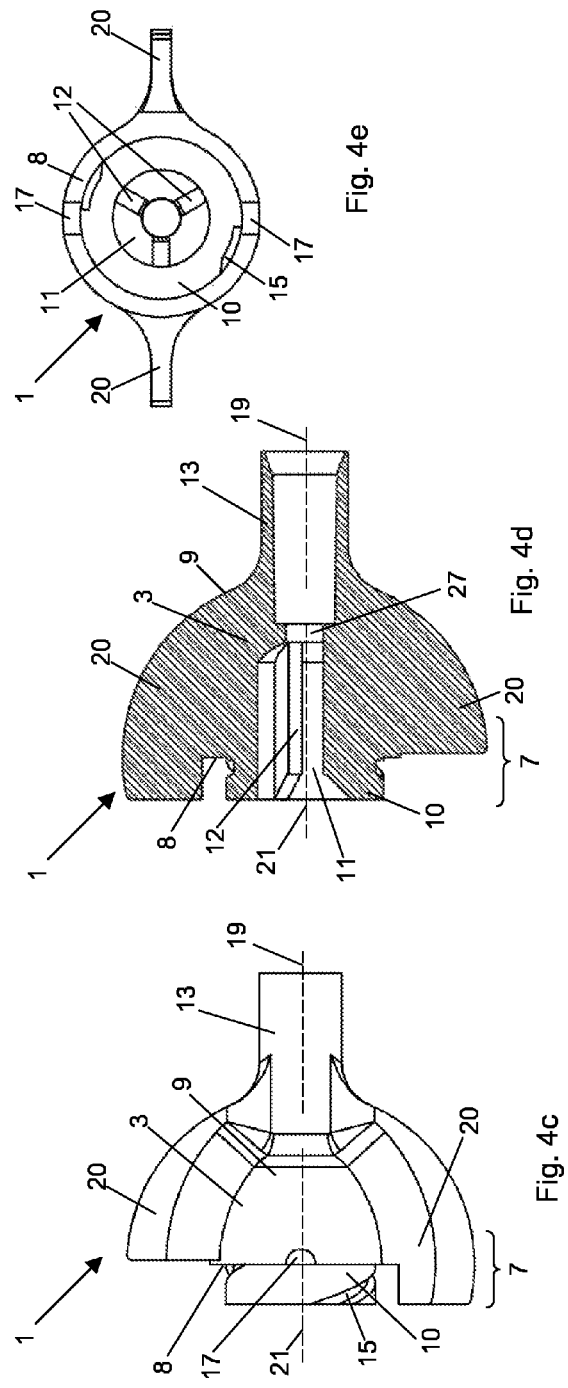

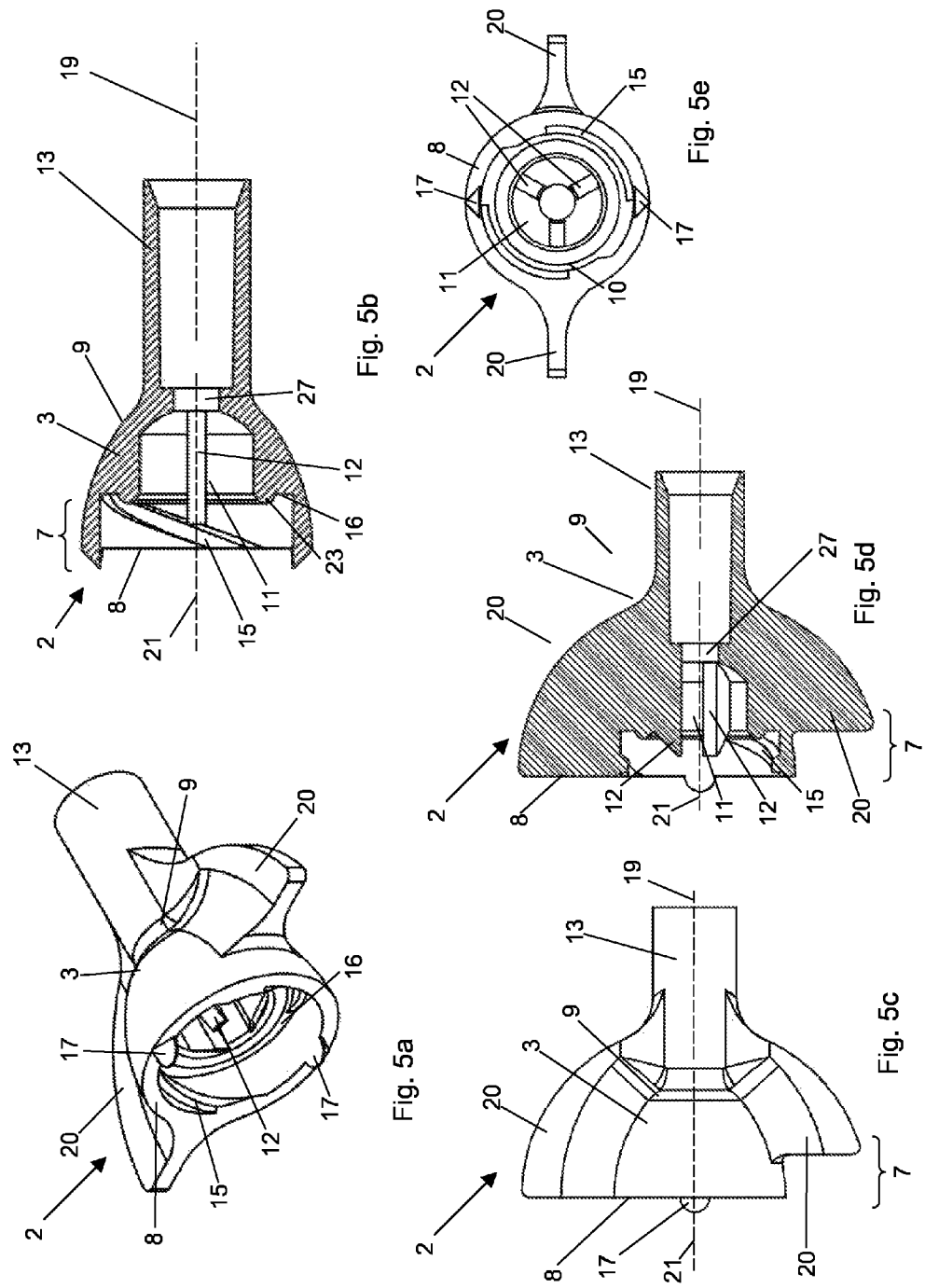

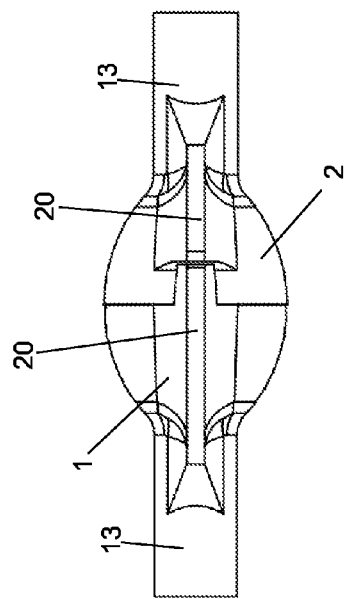
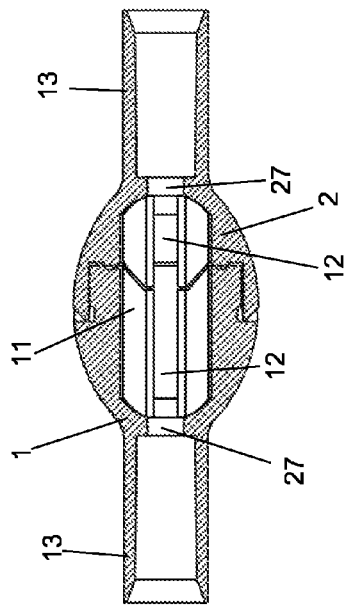
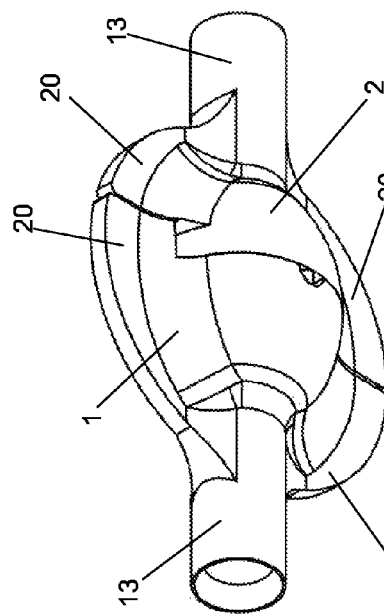
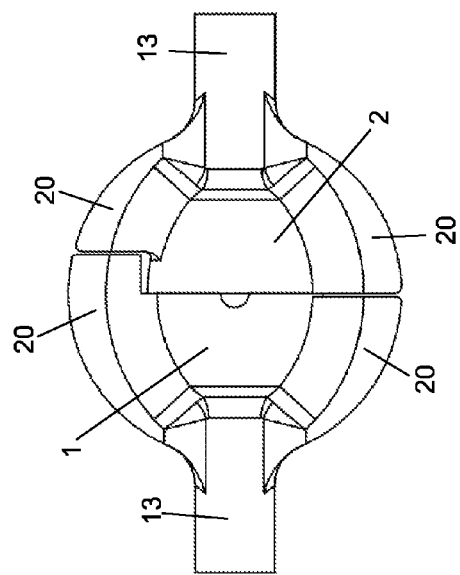
Fig. 6a
Fig. 6b
Fig. 6c
Fig. 6d

MEDICAL CONNECTOR

The present invention relates to a connector for use in fluid driving applications such as enteral feeding sets, catheters, and other medical devices. A connector in the context of this invention is defined as a mechanical device consisting of one of two mating halves and being designed to join a conduit or tube to convey liquids or gases.

BACKGROUND OF THE INVENTION

Hospitals and other medical or healthcare institutions use a variety of catheters, tubing and syringes to deliver medications and other substances to patients through vascular, enteral, respiratory, epidural and intrathecal delivery systems. These delivery systems frequently employ small-bore connectors such as Luer connectors to link various system components. The male and female components of Luer connectors join together to create secure but also detachable leak-proof connections. Multiple connections between medical devices and tubing are common in patient care.

Unfortunately, because Luer connectors are ubiquitous, easy-to-use and compatible between different delivery systems, clinicians can inadvertently connect wrong systems together, causing medication or other fluids to be delivered through the wrong route. Such errors have occurred in diverse clinical settings not only with Luer connectors but also with other small-bore connectors, causing serious patient injuries and deaths.

Significant efforts have been made by healthcare administrations and organizations world-wide to reduce misconnections through education, protocols and monitoring. However, there remains the severe problem that the use of small-bore connectors in incompatible medical delivery systems continues to create situations where dangerous misconnections can, and do, occur.

Thus, there is a strong need for the development of a mechanical solution by medical device manufacturer which prevents misconnections in incompatible medical delivery systems.

SUMMARY OF THE INVENTION

It is therefore the object of the present invention to provide a connector and a connector system for use in fluid driving applications such as enteral feeding sets, catheters and other medical devices which is non-interconnectable with other common medical connectors, fulfils other device requirements for use in a medical environment such as durability, thermostability, rigidity, haptics and the like, is easy to lock and unlock but still ensures a secure connection, and thereby reduces the risk of misconnections as much as possible.

It is another object of the present invention to provide a method of connecting two connectors of a connector system as described above which involves simple connecting steps, is intuitive for a user, employs low connecting forces but still leads to a tight and lasting fit of the connection.

These objects are achieved by the features of the subject matter of claims 1, 11 and 15. Advantageous embodiments of the invention are subject of the subclaims.

According to the invention a connector for use in fluid driving applications such as enteral feeding sets, catheters, and other medical devices, comprises a body having a cylindrical coupling portion with a substantially circular coupling surface, and having an outer surface extending from the coupling surface to form an internal cavity, a tube mating portion extending outward from the body for connecting to a tube, at least one thread sector provided at the coupling portion, and at least one locking means on the coupling surface.

With this connector, the risk of misconnections to other connectors in medical delivery systems is reduced to a minimum merely by its mechanical structure and connecting principle. If forcefully mechanically misconnected to a medical (or other) connector of a different type, its design ensures the absence of a fluid path through the connection. On the other hand, when forcefully inserted into a non-matching bore of a medical delivery device, the cross section of the internal cavity is such that it cannot be penetrated by other standard connectors thereby ensuring a substantial free flow from the source tube to the external environment. A working connection with a non-compatible connector can thus not be achieved.

In addition, when a non-compatible connector is inserted into the internal cavity past the coupling surface of the connector according to the invention, the misconnected embouchure of the non-compatible connector is oriented against an obstacle in the internal cavity, e.g. the bottom or a barrier, which avoids a potential flow. The misconnected embouchure is directly connected to the free atmosphere. It is thus impossible to create a working connection also in this scenario.

It is particularly advantageous that the longitudinal axis of the tube mating portion is substantially orthogonal to the axis of the cylindrical coupling portion. This ensures a maximum of misalignment between the two axes and thus a maximum of incompatibility when the connector according to the invention is wrongfully connected to a medical connector of a different type as described above. Thus, the orientation of the plane of the coupling surface is in this case different from the radial plane of the tube mating portion which makes a forcefully created connection very inefficient.

Alternatively, the axis of the tube mating portion coincides with the axis of the cylindrical coupling portion such that tube mating portion and coupling portion share a common axis.

Thereby, the handling of the connector is greatly enhanced while still ensuring sufficient incompatibility to all other medical connectors.

Preferably, the connector according to the invention is made of rigid material having a modulus of elasticity in flexure or in tension greater than 35 000 kg/cm$^2$ (3433 MPa) or of semi-rigid material having a modulus of elasticity in flexure or in tension between 700 kg/cm$^2$ (69 MPa) and 35 000 kg/cm$^2$ (3433 MPa). The material can be injection molded plastic material. Such material and the manufacturing method of injection molding are well proven and tested in the medical field and thus fulfil a majority of clinical requirements such as durability, thermostability, pressure stability, sterilization and the like. Furthermore, connectors of these materials can be produced in a variety of colors so as to be able to colour-code certain connectors.

In addition, such connector is suited for liquids and gases for a broad range of viscosities, provided that the dimensions of the connector are adapted accordingly. It is preferred for enteral applications to have a minimum inner diameter of 2.4 mm between the tube mating portion and the internal cavity. Depending on the application this diameter may be reduced or increased. The dimensions of the internal volume of the connector according to the invention are designed such that the flow rate through the connector is not slowed down.

It is especially preferred that the internal cavity comprises a plurality of barriers extending from the inner surface of the internal cavity. The barriers prevent that a connector of a different type is able to connect to a connector according to the invention in a fluid-tight manner. Also, any tubing cannot be inserted from the coupling surface side into the internal cavity to provide a tight connection. Thus, the connector of the present invention is again made non-interconnectable with connectors or tubing of a different type. It must be noted that each of the barriers may protrude not only in the radial direction inside the internal cavity but also in an axial direction so as to maximize the incompatibility with other connectors and to minimize a potential flow through such a wrong but forceful connection.

Particularly when the axis of the cylindrical coupling portion and the axis of the tube mating portion coincide, it is advantageous that the connector comprises at least one wing element extending from the body. Such wing elements further prevent misconnections of a connector according to the invention in the whole small bore range, namely diameters up to 15 mm. An effective possibility of a wing structure is e.g. to provide two wings orthogonal to the common axis on either side of the connector, i.e. exactly opposite to each other. The wing element may be formed to provide a good haptic appearance starting at least partially from the outer surface of the tube mating portion up to the plane of the coupling surface or even beyond. This wing configuration is similar to a butterfly or wing nut. Of course more than two wing elements may alternatively be formed on the outside of the body and the tube mating portion.

To provide a "male" connector, the coupling portion of the connector according to the invention preferably comprises a cylindrical extension extending from the coupling surface in a direction away from the body and having an outer diameter which is smaller than the inner diameter of the coupling surface, wherein the at least one thread sector is provided on the outer surface of the cylindrical extension.

In the counterpart "female" connector the at least one thread sector preferably is provided on the inner surface of the coupling portion between the coupling surface and a stop surface positioned inside the internal cavity.

It is understood that the coupling sections, i.e. the portions provided with the thread sectors of the "male" and the "female" connector must fully match and therefore be complementary to each other. Thus, the thread sectors on the outer surface of the cylindrical extension of the "male" connector may protrude from the surface or may be formed as recesses, and correspondingly, the thread sectors on the inside surface of the coupling portion of the "female" connector may be formed as recesses or as protrusions, respectively. Also, the length and number of the thread sectors of the "male" and the "female" connector may be varied thereby determining the length of the rotational locking and releasing movement and the compressive force of the connection.

Preferably, the stop surface of the "female" connector comprises a circular protrusion and/or a sealing face which may be provided by over molding or other manufacturing method. For example, single-shot molding is also possible. A sealing face significantly improves the leak tightness of a connection. An example of a material to be over molded is a thermoplastic elastomer (TPE) sealing layer or face on top of a polypropylene (PP) connector coupling surface. Other suitable materials for the circular protrusion or the sealing face are also possible, e.g. the semi-rigid material polyvinylchloride (PVC). When the stop surface comprises a sealing face then the fluid-tight connection between the "male" and the "female" connector is achieved by the contact of the sealing face with the upper surface of the cylindrical extension of the "male" connector, and not by the contact of the two coupling surfaces. As an alternative to the sealing face or protrusion a sealing gasket such as an o-ring may be position between the upper surface of the cylindrical extension and the stop surface.

Also according to the invention is provided a connector system comprising a first "male" connector and a second "female" connector as described above to provide a fluid-tight connection, wherein the first and second connectors are adapted to be mutually engaged with each other so as to form a mechanically coupled device with the axes of both tube mating portions coinciding or being substantially parallel, wherein (a) the coupling surfaces of each connector are in contact with each other, (b) the at least one thread sector on the outer surface of the cylindrical extension of the first connector is in engagement with the at least one thread sector inside the coupling portion of the second connector, and (c) the locking means on the coupling surface of the first connector is in engagement with the locking means on the coupling surface of the second connector. If the thread sectors of each connector are right-handed threads as is usually the case, then the first "male" connector having the cylindrical extension must be placed substantially in a 90° clockwise offset on top of the second "female" connector having the thread sector in the internal cavity. Rotating the first connector about 90° in a clockwise direction will cause the thread sector(s) of the first connector to engage with thread sector(s) of the second connector until the tube mating portions face away from each other substantially by 180°. This is the final position of the two connectors wherein an optimal flow is ensured from the tube mating portion of the first connector through both internal cavities and canal portions to the tube mating portion of the second connector.

The design of the connector system according to the invention is very user-friendly and implements quick engagement and release kinematics. The haptic appearance supports this by the alignment of the axes of the tube mating portions of the first and the second connector. The compact shape with the preferred rounded edges and the lack of any other sharp edges prevents discomfort for patients also when the connector is used during sleep.

When the "male" connector is combined with the "female" connector the configuration with wing elements as described above is especially preferred. For example, one wing of the "male" connector may extend up to the upper surface plane of the circular extension while the second wing only extends up to the plane of the coupling surface, and one wing of the "female" connector may extend up to the plane of the coupling surface while the second wing only extends up to plane of the stop surface. In such a configuration there is only one possibility to connect the two connectors which is easily grasped by any medical personnel. The resulting connector system provides smooth surfaces thereby demonstrating the correct fit of the two connectors. Furthermore, the wing elements provide optimal points of action to enable a proper disconnecting procedure. It should be noted that alternative configurations of the wing elements may be possible, provided that a complementary wing structure of "male" and "female" connector support the general inventive principle of the invention, i.e. the incompatibility with connectors of a different type and only a perfect fit with the one complementary counterpart.

In the configuration where the axis of the coupling surface is orthogonal to the axis of the tube mating portion it is possible that the tube mating portions of the first and the second connector in the connected position face away from each other or are oriented in the same direction.

Alternatively, in the connector system the at least one locking means in the coupling surface of the first connector is formed as an axial recess and the at least one locking means in the coupling surface of the second connector is formed as an axial protrusion, or the at least one locking means in the coupling surface of the second connector is formed as an axial recess and the at least one locking means in the coupling surface of the first connector is formed as an axial protrusion. This means that the coupling surfaces of the "male" and the "female" connector may comprise one or more complementary protrusions or recesses or a combination thereof to indicate the locking status and to impede any inadvertent releasing of two coupled connectors. It is preferred that the coupling surface of the first "male" connector comprises two recesses and the coupling surface of the second "female" connector comprises the complementary two protrusions, each located at a substantially 90° angle from the axis of the tube mating portion. The protrusions and recesses may be suitably formed to provide an optimum engagement and disengagement procedure. Thus, the shape of the complementary protrusions and recesses determines the engagement and disengagement forces of the connector system.

No further indication of a locking status is thus needed. Accidental disengagements of the two connectors are difficult and improbable. In the configuration where the axes of the tube mating portion and the coupling surface are orthogonal it is particularly difficult because the tube mating portions of the two connectors must rotate in counter-clockwise direction around the coupling axis which is perpendicularly aligned with the tube mating portions against the engagement force of the locking means.

Also for the connector system it is preferred that a sealing gasket such as a rubber ring or o-ring is placed between the first "male" and the second "female" connector, preferably between the stop surface of the "female" connector and the upper surface of the cylindrical extension of the "male" connector. This ensures a fluid tight flow through the connector system.

Also according to the invention is a method of coupling two connectors for use in fluid driving applications such as enteral feeding sets, catheters, and other medical devices, comprising the steps of providing a first "male" and a second "female" connector as described above, arranging the coupling surfaces of the two connectors on top of each other with the axes of each cylindrical coupling portion aligned, and by rotating the two connectors in the plane of their coupling surfaces by a predetermined angle so that the at least one thread sector on the outer surface of the cylindrical extension of the first connector engages with the at least one thread sector inside the coupling portion of the second connector, and the locking means in the coupling surface of the first connector engages with the locking means in the coupling surface of the second connector.

It must be noted that the tube mating portions may comprise any cross-section and shape adapted to be connected to any type of tubing, e.g. elliptical or polygonal. Thus, the circular cross-section and cylindrical shape mostly used throughout this description are only an example.

In addition, the connector or connector system according to the invention provides the following advantages. Due to the innovative design, the connector is clearly distinguishable from every standard connector actually used for healthcare purposes and environments. Colour-coding can easily be implemented by means of commonly available dyes for polymers or other used materials. Furthermore, the smooth outer surface allows for writings, markings and labels to be applied in a simple fashion.

BRIEF DESCRIPTION OF THE DRAWINGS

The above object, features and advantages of the present invention will become apparent from a consideration of the following detailed description presented in connection with the accompanying drawings in which:

FIG. 1a shows a cross section view of a first embodiment of the connector according to the invention;

FIG. 1b shows a first side view of the first embodiment shown in FIG. 1a;

FIG. 1c shows a second side view of the first embodiment shown in FIG. 1a;

FIG. 1d shows a top view of the first embodiment shown in FIG. 1a;

FIG. 2a shows a cross section view of a second embodiment of the connector according to the invention;

FIG. 2b shows a top view of the second embodiment shown in FIG. 2a;

FIG. 2c shows a side view of the second embodiment shown in FIG. 2a;

FIG. 4a shows a perspective view of a third embodiment of the connector according to the invention;

FIG. 4b shows a first cross section view of the third embodiment shown in FIG. 4a;

FIG. 4c shows a side view of the third embodiment shown in FIG. 4a;

FIG. 4d shows a second cross section view of the third embodiment shown in FIG. 4a;

FIG. 4e shows a top view of the third embodiment shown in FIG. 4a;

FIG. 5a shows a perspective view of a fourth embodiment of the connector according to the invention;

FIG. 5b shows a first cross section view of the fourth embodiment shown in FIG. 5a;

FIG. 5c shows a side view of the fourth embodiment shown in FIG. 5a;

FIG. 5d shows a second cross section view of the fourth embodiment shown in FIG. 5a;

FIG. 5e shows a top view of the fourth embodiment shown in FIG. 5a;

FIG. 6a shows a perspective view of the connector system according to the invention with a connector according to the third embodiment of the invention being coupled to a connector according to the fourth embodiment of the invention;

FIG. 6b shows a first side view of the connector system of FIG. 6a;

FIG. 6c shows a second side view of the connector system of FIG. 6a; and

FIG. 6d shows a cross section view of the connector system of FIG. 6a;

DETAILED DESCRIPTION

Figure 3A:
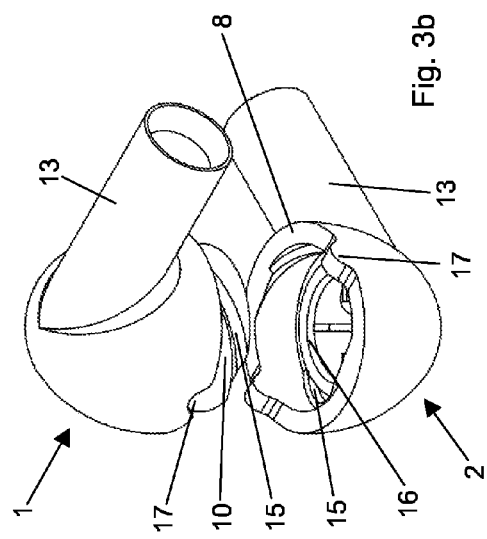
FIGS. 3a, 3b show perspective views of the connector system before a connector according to the first embodiment of the invention is coupled with a connector according to the second embodiment.

FIGS. 1a-1d show a cross section view, a first side view, a second side view, and a top view, respectively, of a first embodiment of the connector according to the invention. The connector 1 which is a "male" connector in this embodiment comprises a body 3 which includes a bottom 5, a cylindrical coupling portion 7 with a substantially circular coupling surface 8 opposite the bottom 5, and an outer surface 9 between the bottom 5 and the coupling surface 8 to form an internal cavity 11. Attached to and extending outward from the outer surface 9 of the body 3 is a tube mating portion 13 which comprises also a cylindrical shape and is adapted to connect to a medical tube being inserted into the tube mating portion 13. Alternatively, the tube mating portion 13 may comprise a non-circular cross section, e.g. an elliptic or polygonal cross-section depending on the tubing to be attached. In the shown embodiment the tube mating portion 13 and the body 3 are positioned in a perpendicular arrangement, i.e. the axis 19 of the tube mating portion 13 and the axis 21 of the cylindrical coupling portion 7 are orthogonal to each other. It is furthermore possible that the attachment angle of the tube mating portion 13 is less than 90° or even 0° meaning that the two axes coincide (see third and fourth embodiment below).

Two thread sectors 15 are provided on the outer surface of a cylindrical extension 10 which protrudes from the coupling surface 8 in a direction away from the bottom 5 and which comprises an outer diameter which is smaller than the inner diameter of the coupling surface 8. The sector angle of the two thread sectors 15 is approximately 160° in the shown first embodiments, but other values of the sector angle are also possible, preferably between approximately 90° and 160°.

Optionally, on the even coupling surface 8 of the body 3 or on the upper surface of the cylindrical extension there may be provided a sealing gasket made of suitable material in order to provide a fluid-tight fit when connected with a second connector as will be described below. A preferred material for the connector 1 according to the invention is an injection molded thermoplastic such as polypropylene (PP) or polyvinylchloride (PVC), vinyls, styrenes and others which fulfil most of the material requirements in the medical field. The sealing gasket can be made of a thermoplastic elastomer (TPE). Depending on the size and the rigidity of the connector material other sealing gasket materials are possible.

As can be seen in FIGS. 1a and 1d, there are four barriers 12 provided in the internal cavity 11 which extend radially from its inner surface into the internal cavity 11. These barriers 12 serve the purpose of impeding the internal cavity from being penetrated by a tube or any other type of non-compatible connector. The end of the barriers 12 in the area of the opening of the cylindrical extension 10 may be flush with the opening plane as depicted in FIGS. 1a -1d. It is alternatively possible that the barriers 12 axially protrude from the opening plane and/or comprise a slanted configuration. It must be noted that the cross section of the internal cavity 11 may assume other shapes such as an elliptical or polygonal shape. A canal portion 27 connects the tube mating portion 13 with the internal cavity 11. The dimension of the canal portion 27 determines the flow rate through the connector 1. This is because the dimensions of the internal cavity 11 or the inside of the tube mating portion 13 are usually larger than the cross section of the canal portion 27.

The two thread sectors 15 on the outer surface of the cylindrical extension 10 are shown as recesses (see FIGS. 1b -1d). Alternatively, they can be formed as protrusions.

The inside of the tube mating portion 13 comprises a circular cross section and a tapered end section where the tubing can be inserted in the connector 1.

It can be seen in FIG. 1c that the body 3 of the connector 1 comprises rounded edges so as to provide a smooth surface without sharp edges for an optimal haptic appearance. Also the transition between the tube mating portion 13 and the cylindrical body 3 comprises rounded portions and no sharp edges.

The coupling surface 8 comprises two locking means 17 formed as recesses which are located at a 90° angle with respect to the axis 19 of the tube mating portion 13. The locking mechanism will be described below.

FIGS. 2a -2c show a cross section view, a top view, and a side view, respectively, of a second embodiment of the connector according to the invention, the "female" connector 2. Most of the features of the "female" connector 2 are identical with the features of the "male" connector 1, therefore only the differences will be described herein.

In the second embodiment two thread sectors 15 are located on the inner surface of the coupling portion 7 from the coupling surface 8 to a stop surface 16 positioned inside the internal cavity 11. Thus, the "female" connector 2 does not comprise a cylindrical extension 10 as the "male" connector 1. The two thread sectors 15 are shown as protrusions (see FIGS. 2a and 2b). Alternatively, they can be formed as recesses. In any case, the thread sectors 15 of the "female" connector 2 must be complementary to the thread sectors 15 of the "male" connector 1.

Furthermore, the barriers 12 formed as radial walls extend only from the stop surface 16 into the internal cavity 11 towards the bottom 5. The stop surface 16 is provided with circular protrusion as a sealing gasket 25 which may be over molded on the material of the connector 2. Alternatively, it is possible to manufacture the circular protrusion 25 by single-shot molding. Also, the stop surface 16 can be left completely flat and a separate sealing gasket may be positioned on the stop surface 16, e.g. by gluing.

Similar to the "male" connector, the barriers 12 of the "female" connector may axially extend beyond the plane of the stop surface 16 and/or may comprise a slanted instead of an even configuration.

Locking means 17 are provided on the coupling surface 8 of connector 2, in the shown embodiment as two protrusions which are located at a 90° angle with respect to the axis 19 of the tube mating portion 13. The shape and position of the two protrusions 17 of the "female" connector 2 is complementary to the shape and position of the two recesses 17 of the "male" connector 1 as will be described below.

Figure 3B:
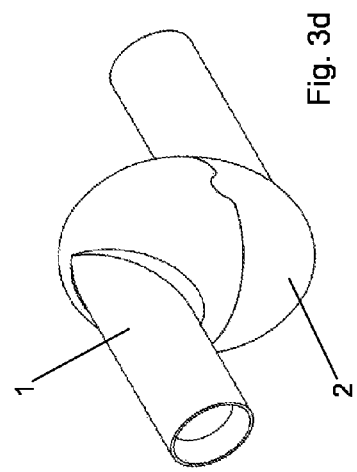
Figure 3C:
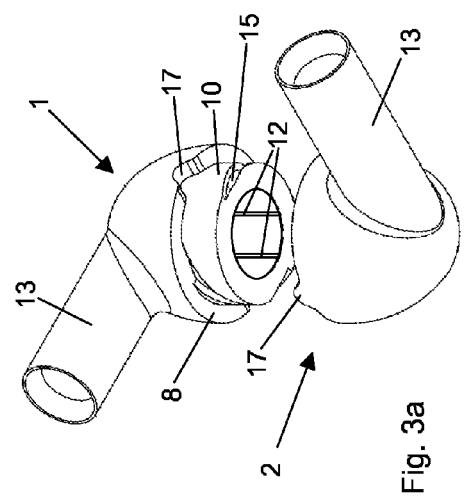
FIGS. 3c, 3d show perspective views of the connector system shown in FIGS. 3a and 3b, respectively, with the two connectors being coupled.
Figure 3D:
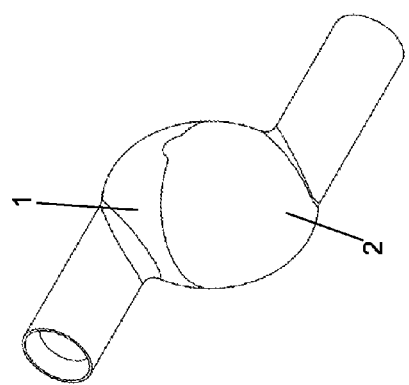

It will now be described with reference to FIGS. 3a -3d how the connectors according to the first and second embodiment can be combined to a connector system which fulfils the majority of requirements in order to avoid misconnections with Luer or other small-bore connectors as described above in the introductory portion.

The "male" connector 1 is able to be mechanically coupled with its counterpart, the "female" connector 2, by a simple kinematic sequence. The method of coupling two connectors comprises the following steps: the coupling surface 8 of the "male" connector 1 is positioned on top of the coupling surface 8 of the "female" connector 2. Optionally, a sealing gasket may be provided between the two connectors to improve the fluid tightness of the connector system as described above. In case that the thread sectors 15 of the "male" connector 1 and the thread sectors 15 of the "female" connector 2 comprise right-handed thread portions as shown in the depicted embodiments, and if the thread sectors 15 are dimensioned as in FIGS. 3a and 3b, then the two connectors 1, 2 must be arranged as shown with the axis 21 of each cylindrical coupling portion 7 aligned and the axis 19 of each tube mating portion 13 in an angular position of 90° with respect to each other. In this position, the coupling surfaces 8 of each connector may be brought close to each other, in case of a sealing gasket or o-ring between them, the respective surfaces are in contact with each side of the sealing gasket or o-ring. In this position the thread sectors 15 of both connectors 1, 2 are ready to engage with each other inside the internal cavity 11 of the "female" connector 2. In order to effect the mechanical coupling of both connectors, one of the two connectors must be rotated in the plane of the coupling surfaces 8 by an angle of approximately 90° in a clockwise direction so that the respective thread sectors 15 engage.

The final locking position is reached by engaging the locking means 17 of the "male" connector 1, in the shown embodiment formed as two recesses arranged at an angle of 90° from the axis 19 of the tube mating portion 13 along the circumference of the coupling surface 8, with the locking means 17 of the "female" connector 2, in the shown embodiment formed as two protrusions arranged at an angle of 90° from the axis 19 of the tube mating portion 13 along the circumference of the coupling surface 8. The protrusions and recesses are designed with rounded edges so that a locking force and, more importantly, a significant releasing force are necessary in order to bring both recess/protrusion pairs into engagement or to release it therefrom.

In the connected position the tube mating portions 13 of both connectors 1, 2 are parallel to each other but face in opposite directions. This will be the preferred way of using the connector system but it is also possible to design both connectors such that the tube mating portions 13 are facing in the same direction when connected. The smooth outer surface of both bodies 3 shows no sharp edges and therefore provides a pleasant haptic appearance of the two connectors in their combined configuration.

As described above, to disengage the two connectors 1 and 2, the tube mating portions 13 must be moved out of their alignment in a counter-clockwise direction so as to release the locking means of the respective connectors. The rotation path must be as far as 90° because only then a full disengagement of the thread sectors is possible. This disengagement procedure means that inadvertent disengagements are very improbable with the connector according to the first and second embodiment, in particular because the axes 19 of the tube mating portions 13 are perpendicular to the rotating plane of the bodies and because of the locking means 17 which have to be disengaged. Pulling at both sides of the tube mating portions 13 alone will therefore not disengage the connectors.

FIGS. 4a-4e show a plurality of views of a connector 1 according to a third embodiment of the invention. This "male" connector 1 comprises a majority of features of the first embodiment described above but differs therefrom in that the axis 21 of the coupling portion 7 is identical with the axis of the tube mating portion 13 and in that the body 3 comprises two wing elements 20 opposite to each other in a configuration similar to a wing nut. Furthermore, there are three barriers 12 within the internal cavity 11 comprising a slanted configuration at the opening of the cylindrical extension 10.

The two wing elements 20 extend from the outer surface 9 of the body 3 and also into the area where the tube mating portion 13 abuts the body 3. The purpose of the wing elements 20 is to provide an ergonomically convenient point of action for the engagement and disengagement of two complementary connectors as will be described below. Therefore, the shown configuration of the third embodiment comprises a smooth transition between the wing elements 20 and the respective elements of the body 3 and the tube mating portion 13.

With respect to FIGS. 4c and 4d it can be seen that the two wing elements 20 are not fully symmetric: one wing element 20 extends just below the plane of the coupling surface 8, and the other wing element 20 extends beyond that plane up to the plane of the opening of the cylindrical extension 10 wherein a gap is provided between the cylindrical extension 10 and the other wing element 20. One of the reasons for this asymmetry is the required mutual engagement with the corresponding "female" connector 2 shown in FIGS. 5a to 5e and will also be apparent from FIGS. 6a to 6d which will be described below. A further reason for the asymmetric wing design is that it prevents misconnections in the small bore range, i.e. up to 15 mm diameter: every potential cross section along a transverse or inclined plane of the connector is greater than 15 mm such that a small bore connection cannot be established.

FIGS. 5a-5e show a plurality of views of a connector 2 according to a fourth embodiment of the invention. This "female" connector 2 comprises a majority of features of the second embodiment described above but differs therefrom in that the axis 21 of the coupling portion 7 is identical with the axis of the tube mating portion 13 and in that the body 3 comprises two wing elements 20 opposite to each other in a configuration similar to a wing nut. Furthermore, there are three barriers 12 within the internal cavity 11 extending beyond the plane of the stop surface 16 and having a slanted configuration. The extension beyond the stop surface 16 has the effect that any tubing or other connector may not be inserted into the canal portion 27 or only in the space between the coupling surface 8 and the stop surface 16. This ensures that only a corresponding complementary "male" connector can effect a useful connection.

The locking means 17 are shaped in the form of a half cone as best seen in FIGS. 5a, 5b, and 5e so as to provide a suitable locking force when coacting with the recesses of the complementary "male" connector.

The two wing elements 20 extend from the outer surface 9 of the body 3 and also into the area where the tube mating portion 13 abuts the body 3. The purpose of the wing elements 20 is to provide an ergonomically convenient point of action for the engagement and disengagement of two complementary connectors as will be described below. Therefore, the shown configuration of the fourth embodiment comprises a smooth transition between the wing elements 20 and the respective elements of the body 3 and the tube mating portion 13.

With respect to FIGS. 5c and 5d it can be seen that the two wing elements 20 are not fully symmetric: one wing element 20 extends up to the plane of the stop surface 16, and the other wing element 20 extends beyond that plane up to the plane of the coupling surface 8.

FIGS. 6a to 6d show a connector system according to the invention with a "male" connector according to the third embodiment of the invention being coupled to a "female" connector according to the fourth embodiment of the invention. Here it can be seen why the respective wing elements 20 comprise an asymmetric configuration for both the "male" and the "female" connectors 1 and 2. It is obvious that only those two complementary connectors may be connected with each other to form a connector system having a smooth surface over the entire coupling area including the ends of the wing elements 20.

The method of engaging or disengaging the "male" and "female" connectors according to the third and fourth embodiment is similar to the method for connecting (or disconnecting) the connectors of the first and second embodiment but essentially differs in that the point of action, i.e. the area where the force is exerted to effect the rotation of the connector(s), is not the tube mating portions but the wing elements 20. Due to the fact that the axes of the coupling portions and the tube mating portions are all identical, the point of action must be located as far away as possible from that central axis. Thus, the wing elements 20 must be oriented in a 90° angle when bringing the coupling surfaces 8 of the "male" and "female" connectors 1, 2 in contact with each other. Then, the rotational force is exerted on the respective wing elements 20 until the engagement of the two connectors by overcoming the locking force of the locking means 17 is effected.

The cross section view of the connector system shown in FIG. 6d demonstrates that the flow rate through the connector system is determined by the size of the canal portion 27 in each connector because the internal cavities 11 of both connectors provide a larger cross section than the cross section of the canal portion 27.

It is to be noted that the number of wing elements 20 can be less or more, if suitably shaped, than in the third and fourth embodiment where the "male" and the "female" connector each comprise two opposite wing elements 20. Furthermore, other types of locking means may be provided on the respective coupling surfaces 8.

With the subject matter of the present invention a connector and a connector system for use in fluid driving applications such as enteral feeding sets, catheters, and other medical devices has been provided which is non-interconnectable with other common medical connectors, fulfils other device requirements for use in a medical environment such as durability, thermostability, rigidity, haptics and others, is easy to lock and unlock but still ensures a secure connection, and thereby reduces the risk of misconnections as much as possible.

LIST OF REFERENCE NUMERALS 1 connector
3 body
5 bottom
7 cylindrical coupling portion
8 coupling surface
9 outer surface
10 cylindrical extension
11 internal cavity
12 barrier
13 tube mating portion
15 thread sector
16 stop surface
17 locking means
19 axis of tube mating portion
20 wing element
21 axis of coupling portion
23 protrusion
25 sealing gasket
27 canal portion

The invention claimed is:

1. A connector (1, 2) for use in fluid driving applications such as enteral feeding sets, catheters, and other medical devices, comprising:
a body (3) having a cylindrical coupling portion (7) with a substantially circular coupling surface (8) and an outer portion (9) extending from the coupling surface (8) to form an internal cavity (11);
a tube mating portion (13) extending outward from the body (3) for connecting to a tube; and
at least one screw thread sector (15) provided at the coupling portion (7) the screw thread sector having a screw axis (21),
wherein at least one locking means (17) is provided on the coupling surface (8), the internal cavity (11) comprising a cylindrical shape is adapted to allow fluid flow therethrough, the coupling surface (8) is adapted to provide a fluid-tight connection in the connected position, and the internal cavity (11) includes a plurality of barriers integral with and extending from the inner surface inside the internal cavity (11), thereby preventing a working connection with a noncompatible connector.

2. The connector (1, 2) of claim 1 wherein the tube mating portion (13) has an axis which is substantially orthogonal to the screw axis (21) of the cylindrical coupling portion (7).

3. The connector (1, 2) of claim 1 wherein the axis (19) of the tube mating portion (13) coincides with the screw axis (21) of the cylindrical coupling portion (7).

4. The connector (1, 2) of claim 1 being made of rigid material having a modulus of elasticity in flexure or in tension greater than 35 000kg/cm$^2$ (3433MPa) or of semi-rigid material having a modulus of elasticity in flexure or in tension between 700kg/cm$^2$ (69MPa) and 35 000kg/cm$^2$ (3433MPa).

5. The connector (1, 2) of claim 4 wherein the material is injection molded plastic material.

6. The connector (1, 2) of claim 1 comprising at least one wing element (20) extending from the body (3).

7. The connector (1) of claim 1 wherein the coupling portion (7) comprises a cylindrical extension (10) extending from the coupling surface (8) in a direction away from the body (3) and having an outer diameter which is smaller than the inner diameter of the coupling surface (8), wherein the at least one thread sector (15) is provided on the outer surface of the cylindrical extension (10).

8. The connector (1, 2) of claim 7 wherein the upper surface of the cylindrical extension (10) comprises a circular protrusion and/or a sealing face.

9. The connector (2) of claim 1 wherein the at least one thread sector (15) is provided on the inner surface of the coupling portion (7) between the coupling surface (8) and a stop surface (16) positioned inside the internal cavity (11).

10. The connector (1, 2) of claim 9 wherein the stop surface (16) or the upper surface of the cylindrical extension (10) comprises a circular protrusion and/or a sealing face.

11. A connector system comprising:
a first connector (1) with a body (3) having a cylindrical coupling portion (7) with a substantially circular coupling surface (8) and an outer portion (9) extending from the coupling surface (8) to form an internal cavity (11);
a tube mating portion (13) extending outward from the body (3) for connecting to a tube; and
at least one thread sector (15) provided at the coupling portion (7), the coupling portion (7) further including a cylindrical extension (10) extending from the coupling surface (8) in a direction away from the body (3) and having an outer diameter which is smaller than the inner diameter of the coupling surface (8), wherein the at least one thread sector (15) is provided on the outer surface of the cylindrical extension (10); and
a second connector (2) with a body (3) having a cylindrical coupling portion (7) with a substantially circular coupling surface (8) and an outer portion (9) extending from the coupling surface (8) to form an internal cavity (11);
a tube mating portion (13) extending outward from the body (3) for connecting to a tube; and
at least one thread sector (15) provided on the inner surface of the coupling portion (7) between the coupling surface (8) and a stop surface (16) positioned inside the internal cavity (11);
wherein at least one locking means (17) is provided on the coupling surface (8), the internal cavity (11) comprising a cylindrical shape is adapted to allow fluid flow therethrough,
wherein the first and second connectors (1, 2) are adapted to be mutually engaged with each other so as to form a mechanically coupled device with the axes (19) of both tube mating portions (13) coinciding or being substantially parallel, wherein:

(a) the coupling surfaces (8) of each connector (1, 2) are in contact with each other to provide a fluid-tight connection,
(b) the at least one thread sector (15) on the outer surface of the cylindrical extension (10) of the first connector (1) is in engagement with the at least one thread sector (15) inside the coupling portion (7) of the second connector (2), and
(c) the locking means (17) on the coupling surface (8) of the first connector (1) is in engagement with the locking means (17) on the coupling surface (8) of the second connector (2).

12. The connector system of claim 11 wherein the at least one locking means (17) on the coupling surface (8) of the first connector (1) is formed as an axial recess and the at least one locking means (17) on the coupling surface (8) of the second connector (2) is formed as an axial protrusion.

13. The connector system of claim 11 wherein the at least one locking means (17) on the coupling surface (8) of the second connector (2) is formed as an axial recess and the at least one locking means (17) on the coupling surface (8) of the first connector (1) is formed as an axial protrusion.

14. The connector system of claim 11 wherein a sealing gasket (25) such as a rubber ring is placed between the coupling surfaces (8) of the first and the second connector (1, 2).

15. A method of coupling two connectors (1, 2) for use in fluid driving applications such as enteral feeding sets, catheters, and other medical devices, comprising:
 providing a first connector (1) with a body (3) having a cylindrical coupling portion (7) with a substantially circular coupling surface (8) and an outer portion (9) extending from the coupling surface (8) to form an internal cavity (11);
 a tube mating portion (13) extending outward from the body (3) for connecting to a tube; and
 at least one thread sector (15) provided at the coupling portion (7), the coupling portion (7) further including a cylindrical extension (10) extending from the coupling surface (8) in a direction away from the body (3) and having an outer diameter which is smaller than the inner diameter of the coupling surface (8), wherein the at least one thread sector (15) is provided on the outer surface of the cylindrical extension (10); and
 providing a second connector (2) with a body (3) having a cylindrical coupling portion (7) with a substantially circular coupling surface (8) and an outer portion (9) extending from the coupling surface (8) to form an internal cavity (11);
 a tube mating portion (13) extending outward from the body (3) for connecting to a tube; and
 at least one thread sector (15) provided on the inner surface of the coupling portion (7) between the coupling surface (8) and a stop surface (16) positioned inside the internal cavity (11);
 wherein at least one locking means (17) is provided on the coupling surface (8), the internal cavity (11) comprising a cylindrical shape is adapted to allow fluid flow therethrough,
 arranging the coupling surfaces (8) of the two connectors (1, 2) on top of each other with the axes (21) of each cylindrical coupling portion (7) aligned, and by rotating the two connectors (1, 2) in the plane of their coupling surfaces (8) by a predetermined angle so that the at least one thread sector (15) on the outer surface of the cylindrical extension (10) of the first connector (1) engages with the at least one thread sector (15) inside the coupling portion (7) of the second connector (2), and the locking means (17) in the coupling surface (8) of the first connector (1) engages with the locking means (17) in the coupling surface (8) of the second connector (2), wherein the coupling surface (8) of the first connector (1) and the coupling surface (8) of the second connector (2) are in contact with each other to achieve a fluid-tight connection.

\* \* \* \* \*